| United States Patent [19] | [11] 4,038,305 |
|---|---|
| Eliasson et al. | [45] July 26, 1977 |

[54] CYCLOPENTENONE DERIVATIVES

[75] Inventors: Rune Eliasson, Vallingby, Sweden; Poul Nedenskov, Birkerod, Denmark

[73] Assignee: Aktieselskabet Grindstedvaerket, Arhus, Denmark

[21] Appl. No.: 617,774

[22] Filed: Sept. 29, 1975

Related U.S. Application Data

[63] Continuation-in-part of Ser. No. 341,660, March 15, 1973, abandoned.

[30] Foreign Application Priority Data

Mar. 20, 1972 United Kingdom ............... 12941/72

[51] Int. Cl.$^2$ ...................... C07C 61/38; C07C 69/74

[52] U.S. Cl. .............................. 260/468 K; 260/347.3; 260/347.5; 260/413; 260/410.8 R; 260/468 D; 260/514 D; 260/514 K; 424/305; 424/317

[58] Field of Search .......... 260/468 D, 468 K, 514 D, 260/514 K, 69

[56] References Cited

U.S. PATENT DOCUMENTS

3,808,258  4/1974  Bagli et al. .......................... 260/468

*Primary Examiner*—Robert Gerstl
*Attorney, Agent, or Firm*—Lawrence Rosen; E. Janet Berry

[57] ABSTRACT

This invention relates to novel cyclopentenone derivatives having valuable biological properties, and to a process for producing the same.

2 Claims, No Drawings

CYCLOPENTENONE DERIVATIVES

This application is a continuation-in-part of our application Ser. No. 341,660, filed Mar. 15, 1973, now abandoned. The present invention relates to novel cyclopentenone derivatives having valuable biological properties.

More particularly, the invention relates to compounds of the formula

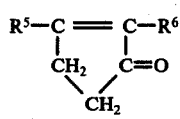

(I)

wherein $R^5$ is —$(CH_2)_7$—$COOR^7$, when $R^6$ is —OH or —$OCOR^4$, each of $R^4$ and $R^7$ representing hydrogen or an alkyl group having 1–8 carbon atoms, and $R^5$ is hydrogen or the group

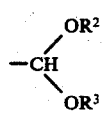

(II)

wherein $R^2$ and $R^3$ are alkyl groups of 1–8 carbon atoms, when $R^6$ is a group of the formula —$(CH_2)_6$—$COOR^1$, wherein $R^1$ is an alkyl group having 1–8 carbon atoms.

The compounds of the invention have a prostaglandinlike effect upon the human uterus. Thus, an inhibiting effect on the spontaneous motility of the myometrium from non-pregnant women has been observed in vitro, the $ID_{50}$ being 50 μg/ml in the tests carried out as described by M. Bygdeman and R. Eliasson in Acta physiol. Scand. 1963, 59, 43–51. This is indicative of fertility activating properties, when administered in doses of between 0.5 and 10 mg/kg, where the infertility is due to too low activity of the prostaglandins in the semen.

Besides having pharmaceutically useful properties, the compounds of this type are also useful as intermediates in the synthesis of prostaglandins and other prostaglandin type compounds, e.g. according to the following scheme of reactions:

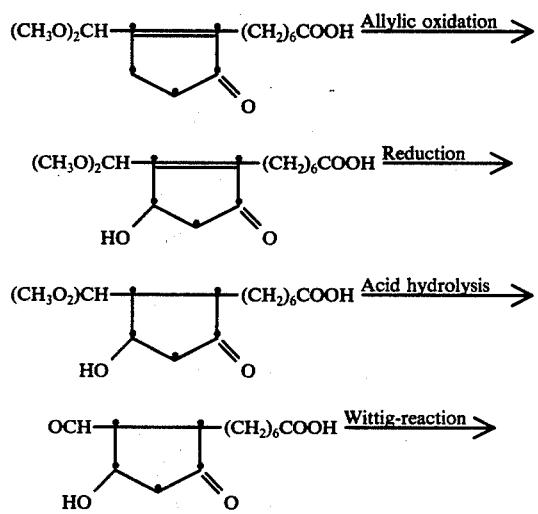

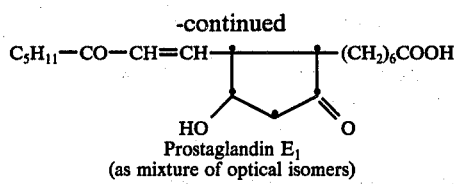

Prostaglandin E₁
(as mixture of optical isomers)

The cyclopentenone derivatives of the invention are prepared by subjecting a compound of the formula

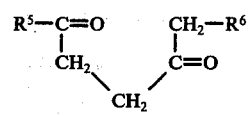

(III)

wherein $R^5$ and $R^6$ are as hereinbefore defined, to a dehydrating ring closure in the presence of a base, and recovering the resulting compound of formula I.

If the resulting product is an acid, it can be esterified with an alcohol, or a reactive derivative thereof, such as a diazoalkane. If it is an ester, it can be saponified to the free acid. In both cases, known methods suitable for the purpose can be applied.

The dehydrating process to yield the cyclopentenone derivative is preferably carried out in water or methanol in the presence of an alkali hydroxide or alkali alkoxide, respectively.

The starting compounds for the above mentioned reaction have not previously been described in the literature. Their preparation is described in our co-pending application Ser. No. 341,627, filed Mar. 15, 1973, starting from 8-(2-furyl)-octanoic acid of the formula:

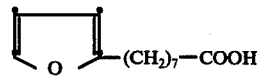

or an ester thereof, which is formylated according to Vilsmeier to introduce a formyl group in the 5-position of the furan ring, said group being converted into an acetal group or an acyloxymethyl group, if desired, the resulting furyl compound being electrolytically oxidized in the presence of methanol to the corresponding 2,5-dimethoxy-dihydrofuryl compound, which is catalytically hydrogenated to yield a desired starting material for preparing a compound according to the present invention.

The following Examples are illustrative of the compounds of the invention, and their preparation:

EXAMPLE 1

8-(2-Hydroxy-3-oxo-1-cyclopenten-1-yl)-octanoic acid

Nitrogen gas was bubbled through 50 ml of an aqueous 2% potassium hydroxide solution for 30 minutes, after which 500 mg of 13-acetoxy-9,12 dioxotridecanoic acid methyl ester were added. The mixture was heated to 95° C for 1 hour under nitrogen. The solution was then cooled and purified by washing with ether. The aqueous solution was acidified and extracted with ether. The combined ether solutions were dried, and the ether was driven off to yield an oil. The oil was extracted with 20 ml of boiling benzene, and 70 mg of a brown, oily material were removed by filtration. Petroleum ether (35 ml) was added to the benzene solution.

On cooling, the desired compound was obtained in the form of crystals having a melting point of 99-101° C.

Analysis: Calculated: C 65.0, H 8.4
Found : C 64.7 H 8.3%.

EXAMPLE 2

7-(2-Dimethoxymethyl-5-oxo-1-cyclopenten-1-yl)-heptanoic acid methyl ester.

To a solution of sodium methoxide in methanol, prepared from 0.52 g of sodium and 90 ml of methanol, were added 5.68 g of a mixture containing about 5.28 g of 13,13-dimethoxy-9,12-dioxotridecanoic acid methyl ester.

The solution was left at room temperature under nitrogen for 14 hours, following which the product was isolated by the method described in Example 1. An oil was obtained having a boiling point of 160-164° C at 0.07 mm Hg.

Analysis: Calculated: C 64.4, H 8.8, methoxyl 31.2
Found : C 64.1 H 8.7 methoxyl 31.0%.

EXAMPLE 3

7-(5-Oxo-1-cyclopenten-1-yl)-heptanoic acid methyl ester

To a solution of sodium methoxide in methanol, prepared from 0.29 g of sodium and 50 ml of methanol, were added 2.42 g of 11-formyl-9-oxo-undecanoic acid methyl ester.

The solution was left under nitrogen at room temperature for 14 hours, following which it was cooled to 0° C and neutralized with acetic acid. The mixture was evaporated to dryness under vacuum. 40 ml of ice water were then added, whereupon the mixture was extracted with ether. The ether extract was washed with an aqueous solution of sodium bicarbonate and then dried.

Evaporation of the ether and distillation yielded an oil having a boiling point of 121°-124° C at 0.08 mm Hg.

Analysis: Calculated: C 69.6, H 9.0, methoxyl 13.8
Found: C 69.3 H 9.0, methoxyl 13.9%.

We claim:

1. Cyclopentenone derivatives of the formula

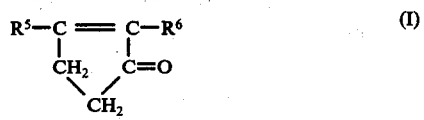

wherein $R^5$ is the group

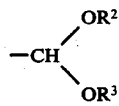

wherein each of $R^2$ and $R^3$ is an alkyl group of 1-8 carbon atoms, when $R^6$ is a group of the formula $-(CH_2)_6-COOR^1$, wherein $R^1$ is an alkyl group having 1-8 carbon atoms.

2. A cyclopentenone derivative of the formula

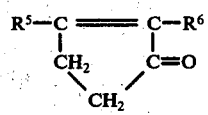

in which $R^5$ is a dimethoxymethyl group and $R^6$ is the group $-(CH_2)_6-COOCH_3$.

* * * * *